US011597695B2

(12) United States Patent
Kolk et al.

(10) Patent No.: US 11,597,695 B2
(45) Date of Patent: Mar. 7, 2023

(54) METHOD OF PREPARING HYDROXYALKYLCARBOXYLIC ACID ESTERS

(71) Applicant: BASF SE, Ludwigshafen am Rhein (DE)

(72) Inventors: Miriam Kolk, Düsseldorf-Holthausen (DE); Konstantinos Scholinakis, Düsseldorf-Holthausen (DE); Eike Ulf Mahnke, Düsseldorf-Holthausen (DE); Lutz Hilterhaus, Düsseldorf-Holthausen (DE); Volker Winterhoff, Düsseldorf-Holthausen (DE)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 16/340,788

(22) PCT Filed: Oct. 11, 2017

(86) PCT No.: PCT/EP2017/075890
§ 371 (c)(1),
(2) Date: Apr. 10, 2019

(87) PCT Pub. No.: WO2018/069372
PCT Pub. Date: Apr. 19, 2018

(65) Prior Publication Data
US 2020/0048180 A1 Feb. 13, 2020

(30) Foreign Application Priority Data

Oct. 12, 2016 (EP) .................................... 16193441

(51) Int. Cl.
*C07C 67/08* (2006.01)
*C07C 69/68* (2006.01)
(52) U.S. Cl.
CPC .............. *C07C 67/08* (2013.01); *C07C 69/68* (2013.01)
(58) Field of Classification Search
CPC ...................................................... C07C 67/08
USPC ........................................................ 560/176
See application file for complete search history.

(56) References Cited

U.S. PATENT DOCUMENTS

| 6,271,410 B1* | 8/2001 | John ................. C07C 253/30 558/443 |
| 2005/0032653 A1* | 2/2005 | Kunz ................ C10M 107/36 508/216 |
| 2012/0103790 A1 | 5/2012 | Krull |
| 2015/0291634 A1* | 10/2015 | Bell ................. C07C 29/1285 556/470 |

FOREIGN PATENT DOCUMENTS

| CN | 103739489 | * | 4/2014 |
| WO | 2005049556 A2 | | 6/2005 |
| WO | 2008098581 A1 | | 8/2008 |

OTHER PUBLICATIONS

Treptow et al. Journal of the American Oil Chemists' Society (2016), 93(10), 1399-1406.*
Machine transaltion CN N 103739489 2014.*
Hu , Huagong Shikan (2013), 27(1), 25-27.*
International Search Report for International Application No. PCT/EP2017/075890, dated Feb. 6, 2018, 4 pages.
Written Opinion of the International Searching Authority for International Application No. PCT/EP2017/075890, dated Feb. 6, 2018, 6 pages.
Asthana, et al., "A Kinetic Model for the Esterification of Lactic Acid and Its Oligomers", Industrial & Engineering Chemistry Research, vol. 45, Issue 15, 2006, pp. 5251-5257.
Fabian, et al., "Efficient Microwave-Assisted Esterification Reaction Employing Methanesulfonic Acid Supported on Alumina as Catalyst", Synthetic Communications, vol. 44, Issue 16, 2014, pp. 2386-2392.
Kumar, et al., "A Facile Conversion of Halides. Alcohols and Olefins to Esters Usihg Iron(III) Perchlorate", Synthetic Communications, vol. 22, Issue 7, 1992, pp. 1087-1094.
Liang, et al., "Fe2(SO4)3·4H2O/concentrated H2SO4: an efficient catalyst for esterification", Journal of Chemical Research, vol. 2004, Issue 3, Mar. 2004, pp. 226-227.
Vu, et al., "Oligomer distribution in concentrated lactic acid solutions", Fluid Phase Equilibria, vol. 236, Issue 1-2, Sep. 20, 2005, pp. 125-135.

* cited by examiner

*Primary Examiner* — Ana Z Muresan
(74) *Attorney, Agent, or Firm* — Armstrong Teasdale LLP

(57) ABSTRACT

A method of preparing an ester by reacting a carboxylic acid with a ($C_1$-$C_{36}$)alcohol in the presence of a catalyst that is suitable for preparing carboxylic acid esters of monomeric carboxylic acids in high yield. The method reduces by-products of the reaction, in particular esters of dimeric, trimeric and/or oligomeric carboxylic acids. The method requires a minimal excess of alcohol and does not require removal of water and/or carboxylic acid ester from the reaction mixture. The method is particularly suitable for the reaction of hydroxyalkylcarboxylic acids and fatty alcohols.

15 Claims, No Drawings

METHOD OF PREPARING HYDROXYALKYLCARBOXYLIC ACID ESTERS

CROSS-REFERENCE TO RELATED APPLICATIONS

This application is a U.S. National Phase Application of PCT/EP2017/075890, filed Oct. 11, 2017, which claims the benefit of priority to EP Application No. 16193441.9, filed Oct. 12, 2016, the contents of which are hereby expressly incorporated by reference in their entirety.

The present invention relates to a method of preparing an ester by reacting a carboxylic acid with a $(C_1-C_{36})$alcohol in the presence of a catalyst. The method is particularly suitable for reacting hydroxyalkylcarboxylic acids with fatty alcohols.

Carboxylic acid esters can be obtained by eliminating water from carboxylic acids and alcohols or by transesterification of another suitable carboxylic acid ester. The direct reaction of a carboxylic acid and an alcohol usually only proceeds very slowly. The addition of catalysts such as acids accelerates the esterification.

However, the thermodynamic equilibrium of the esterification reaction of carboxylic acids and alcohols is often unfavourable such that the esterification in the presence of acids requires a significant excess of alcohol and the reaction products (water and/or ester) are removed from the reaction mixture in order to increase the yield of the desired product.

Even without addition of an external acid, the esterification of hydroxyalkylcarboxylic acids such as the esterification of lactic acid or citric acid proceeds sufficiently rapidly because the reaction proceeds autocatalytically. As a result of the law of Mass action, a high concentration of the starting materials as well as a low concentration of water is advantageous for the esterification of these carboxylic acids in order to accomplish a high yield. Therefore, it is generally preferred that the carboxylic acid is used in a concentration as high as possible and with a low water content. However, the monomeric forms of some hydroxyalkylcarboxylic acids such as lactic acid tend to form dimers, trimers and/or oligomers at higher concentrations which reduces the yield of the desired product. Dimers, trimers and oligomers (D. T. Vu et al., *Fluid Phase Equilibria* 2005, 236, 125-135) as well as the lactones are known to form by means of autocatalytic intermolecular esterification at high concentration by intramolecular esterification. The equilibrium of monomeric lactic acid (A) to the dimeric (B), trimeric (C) and oligomeric lactic acid (D, q>2) is illustrated in the following scheme:

Thus, in the esterification of 88 wt.-% aqueous lactic acid, also dimeric, trimeric and oligomeric lactic acid esters are formed. This reaction is less pronounced at lower concentrations and is no longer observed at 20 wt.-% aqueous lactic acid (N. S. Asthana et al., *Ind. Eng. Chem. Res.* 2006, 45, 5151-5257). However, using aqueous lactic acid solutions at low concentrations is usually not economically reasonable.

Thus, it is one object of the present invention to provide a method that is suitable for preparing carboxylic acid esters of monomeric carboxylic acids in high yield.

Furthermore, it is an object of the invention to reduce the by-products of the reaction, in particular the esters of dimeric, trimeric and/or oligomeric carboxylic acids. A further object of the present invention is to provide a method that requires an excess of the alcohol as low as possible and at the same time does not require removal of water and/or carboxylic acid ester from the reaction mixture.

DESCRIPTION OF THE INVENTION

The invention relates to a method of preparing an ester by reacting a carboxylic acid of formula (I)

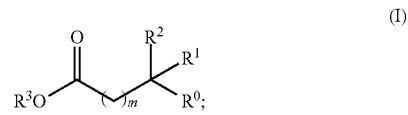

wherein
$R^0$ is —H or —$OR^3$ is;
$R^1$ is —H, —$(C_1-C_6)$alkyl, —$(C_1-C_6)$alkylCOOR$^3$, —COOR$^3$ or —OR$^3$;
$R^2$ is —H, —$(C_1-C_6)$alkyl, —$(C_1-C_6)$alkylCOOR$^3$ or $(C_6-C_{10})$aryl, wherein $R^2$ is optionally substituted with —OR$^3$ and/or —COOR$^3$;
$R^3$ is —H or —$(C_1-C_6)$alkyl;
m is 0, 1, 2, 3, 4 or 5;
and a $(C_1-C_{36})$alcohol, that is optionally substituted with a substituent from the group consisting of —CN, -halogen, —$(C_2-C_6)$alkenyl and —$(C_2-C_6)$alkynyl;
wherein the reaction is carried out in the presence of a catalyst.

Surprisingly, carboxylic acid esters can be obtained in high yields by reacting the carboxylic acid of general formula (I) and a $(C_1-C_{36})$alcohol in the presence of a catalyst.

The increased yields are accompanied by the reduction of the undesired by-products such as the esters of the respective dimers, trimers, and/or oligomers of hydroxyalkylcarboxylic acids.

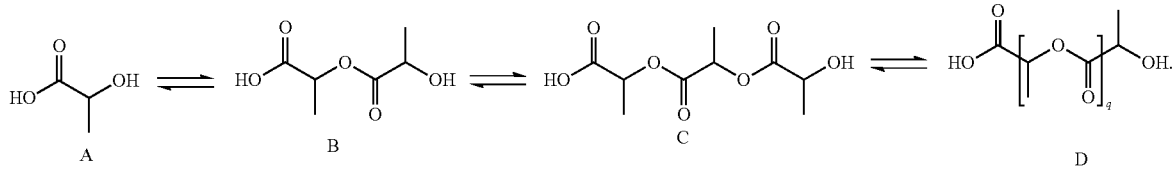

Therefore, in the reaction of, for instance, lactic acid with $(C_1-C_{36})$alcohols not only the esters of monomeric lactic acid are formed, but also the respective esters of the dimeric, trimeric, and oligomeric lactic acid which are likewise undesired and optionally have to be removed from the desired product.

Thus, 88 wt.-% aqueous lactic acid, for instance, consists of a molar portion of 86.77% of monomer, 11.26% dimer and 1.98% trimer with the rest being oligomeric lactic acid. The autocatalytic esterification with the $(C_1-C_{36})$alcohol 2-ethylhexanol results in a molar portion of about 86.76% of the desired 2-ethylhexyl lactate in the reaction mixture. In this autocatalytic reaction, the equilibrium of the monomer and the dimer, trimer and oligomer can essentially not be influenced and the ratio of the ester of the monomer and the dimer, trimer and oligomer roughly corresponds to the ratio of the monomeric lactic acid and the dimers, trimers and oligomers before the reaction.

When the reaction of the carboxylic acid of formula (I) is carried out with a catalyst according to the invention, the portion of the desired monomeric carboxylic acid ester can be increased. For instance, in the reaction of lactic acid in the presence of a catalyst according to the invention, such as for instance 2-hydroxyethylsulfonic acid, the molar portion of the monomeric ester is 96.25%. Thus, in the presence of the catalyst, the dimer, trimer and oligomer of lactic acid hydrolyse to the monomer which results in a higher portion of the monomeric lactic acid ester. The catalyst hence allows the reaction of a carboxylic acid of general formula (I) also at a lower temperature which results in a reduced consumption of energy. On the other hand, the presence of the catalyst results in an increased yield of the desired monomeric carboxylic acid ester.

In an embodiment according to the invention, the carboxylic acid of formula (I)

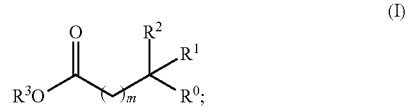

(I)

wherein
$R^0$ is —H or —OR$^3$;
$R^1$ is —H, —(C$_1$-C$_6$)alkyl, —(C$_1$-C$_6$)alkylCOOR$^3$, —COOR$^3$ or —OR$^3$; and
$R^2$ is —H, —(C$_1$-C$_6$)alkyl, —(C$_1$-C$_6$)alkylCOOR$^3$ or (C$_6$-C$_{10}$)aryl, wherein $R^2$ is optionally substituted with —OR$^3$ and/or —COOR$^3$;
$R^3$ is —H or —(C$_1$-C$_6$)alkyl; and
m is 0, 1, 2, 3, 4 or 5.
m is 0 or 1.

In a preferred embodiment of the invention, the carboxylic acid is a hydroxyalkylcarboxylic acid of formula (II):

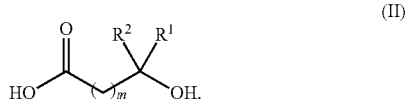

(II)

In a preferred embodiment of the invention, the carboxylic acid is a hydroxyalkylcarboxylic acid of formula (II), wherein m is 0 or 1.

In a preferred embodiment of the invention, the carboxylic acid is a hydroxyalkylcarboxylic acid of formula (II), wherein $R^1$ is —H or —(C$_1$-C$_6$)alkyl.

In a preferred embodiment of the invention, the carboxylic acid is glycolic acid, lactic acid, tartaric acid, citric acid, isocitric acid, mandelic acid, or malic acid.

If the carboxylic acids of formula (I) or (II) have a stereogenic carbon atom, they can be present in the D-configuration, the L-configuration, the meso-configuration or as a mixture of these configurations. The L-configuration is preferred.

In a particularly preferred embodiment of the invention, the carboxylic acid is lactic acid.

In a particularly preferred embodiment of the invention, the carboxylic acid is L-lactic acid.

The esterification of carboxylic acids of formula (I) is carried out with (C$_1$-C$_{36}$)alcohols. The (C$_1$-C$_{36}$)alcohol can be a fatty alcohol. The fatty alcohols can be present in saturated or unsaturated form.

In an embodiment of the invention, the (C$_1$-C$_{36}$)alcohol is unsaturated linear fatty alcohol.

In an embodiment of the invention, the (C$_1$-C$_{36}$)alcohol is a saturated linear fatty alcohol.

In an embodiment of the invention, the (C$_1$-C$_{36}$)alcohol is an unsaturated branched fatty alcohol.

In an embodiment of the invention, the (C$_1$-C$_{36}$)alcohol is saturated branched fatty alcohol.

Preferred fatty alcohols comprise cis-9-hexadecene-1-ol, trans-9-octadecene-1-ol, cis-9-octadedene-1-ol, 1-decanol, 1-hexadecanol, 1-heptadecanol, 1-octadecanol, 2-propyl-4-methyl-hexanol, 2-propyl-5-methylhexanol, 2-iso-propyl-4-methylhexanol, 2-iso-propyl-5-methylhexanol, 2-propyl-4,4-dimethylhexanol, 2-ethyl-2-methylheptanol or 2-ethyl-2,5-dimethylhexanol.

In another embodiment of the invention, the (C$_1$-C$_{36}$) alcohol is a (C$_6$-C$_{36}$)Guerbet alcohol of the following formula (VI)

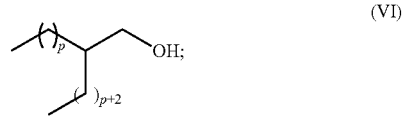

(VI)

wherein p is 0, 1, 2, 3, 4, 5, 6, 7, 8, 9, 10, 11, 12, 13, 14, 15 or 16, preferably p is 0, 1, 2, 3 or 4, more preferably p is 1 or 2.

In an embodiment of the invention (C$_1$-C$_{36}$)alcohol is a (C$_8$-C$_{12}$) Guerbet alcohol.

Preferred C$_6$-C$_{36}$ Guerbet alcohols comprise 2-methyl-1-pentanol (p=0), 2-ethyl-1-hexanol (p=1), 2-Propyl-1-heptanol (p=2), 2-Butyl-1-octanol (p=3), 2-Pentyl-1-nonanol (p=4), 2-hexyl-1-decanol (p=5), 2-heptyl-1-undecanol (p=6) or 2-Octyl-1-dodecanol (p=7).

In a particularly preferred embodiment, the (C$_1$-C$_{36}$) alcohol is 2-ethyl-1-hexanol.

As discussed before, catalysts are used for the esterification of carboxylic acids in order to accelerate the shift of the equilibrium. Hydroxyalkylcarboxylic acids also react in the absence of an external catalyst in a sufficiently rapid manner as the hydroxyalkylcarboxylic acids act as autocatalysts. However, this autocatalytic esterification of hydroxyalkylcarboxylic acids also results in undesired by-products (for instance dimers and trimers of the hydroxyalkylcarboxylic acids). Using the catalysts according to the invention favours hydrolysis of the dimeric or trimeric hydroxyalkylcarboxylic acid esters to monomeric carboxylic acids and thus allow the more specific conversion of the monomeric hydroxyalkylcarboxylic acid to the desired product. Thus, in the reaction of lactic acid and 2-ethylhexanol in the presence of a catalyst according to the invention, for instance, the portion of the monomeric ester can be increased from about 86.76% to 96.25%.

In an embodiment of the invention, the catalyst is a compound of formula (V) or a salt thereof

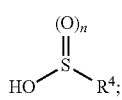

(V)

wherein
R⁴ is —(C₁-C₆)alkyl, —OH, —NH₂ or —(C₁-C₆)alkyl-COOR³, wherein R⁴ is optionally substituted with —OH; and
n is 1 or 2.

In an embodiment of the invention, the catalyst is a compound of formula (V), wherein
R⁴ is —(C₁-C₆)alkyl, wherein R⁴ is optionally substituted with —OH; and
n is 2.

In an embodiment of the invention, the catalyst is a compound of formula (V), wherein
R⁴ is —(C₁-C₆)alkyl, wherein R⁴ is substituted with —OH; and
n is 2.

In an embodiment of the invention, the catalyst is selected from the list consisting of 1-hydroxyethanesulfonic acid, 2-hydroxyethanesulfonic acid, methanesulfonic acid, aluminium mesylate, sulfosuccinic acid and amidosulfuric acid. 2-hyxdroxyethanesulfonic acid is preferred.

In an embodiment of the invention, the catalyst is a salt or oxide of metal M, wherein M is Sn, Zn, Ti, Zr, Bi, Fe, Ag or Al.

In an embodiment of the invention, the catalyst is a salt comprising a kation consisting of the group $Sn^{2+}$, $Zn^{2+}$, $Ti^{4+}$, $Zr^{4+}$, $Bi^{3+}$, $Fe^{2+}$, $Fe^{3+}$, $Ag^+$ and $Al^{3+}$. Suitable anions of these salts can for instance be selected from the group consisting of $Cl^-$, $F^-$, $Br^-$, $I^-$, $^-O(C_1-C_{36})alkyl$, $^-OOC(C_1-C_{36})alkyl$, oxalate, mesylate, triflate, $CO_3^{2-}$, acetate, malonate, tartrate, citrate, and lactate.

In a preferred embodiment of the invention, the catalyst is a salt comprising the group consisting of aluminium mesylate, tin-bis(2-ethylhexanoate), tin(II)oxalate, tin(II)chloride, tin(II)chloride dihydrate, tetra-iso-propyltitanate, tetra-n-butyltitanate, tetra-2-ethyl-hexyltitanate, polybutyltitanate, iso-propyl-n-butyltitanate, tetra-n-propyltitanate, tetra-ethyltitanate, tetra-t-butyltitanate, tetra-n-propylzirconate, tetra-n-butylzirconate and bismuth triflate.

In a preferred embodiment of the invention, the catalyst is an oxide comprising the group consisting of tin(II)oxide.

In a preferred embodiment of the invention, the catalyst is aluminium mesylate or tin-bis(2-ethylhexanoate).

In an embodiment of the invention, the formed ester is a compound of formula (III):

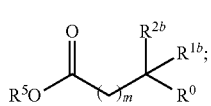

(III)

wherein
R⁰ is —H or —OR³;
R^{1b} is —H, —(C₁-C₆)alkyl, —(C₁-C₆)alkylCOOR⁶, —COOR⁶ or —OR³;
R^{2b} is —H, —(C₁-C₆)alkyl or —(C₁-C₆)alkylCOOR⁶, wherein R^{2b} is optionally substituted with —OR³ and/or —COOR⁶;

R³ is —H or —(C₁-C₆)alkyl;
m is 0, 1, 2, 3, 4, 5 or 6;
R⁵ is —(C₁-C₃₆)alkyl optionally substituted with a substituent of the group comprising —CN, -halogen, —(C₂-C₆)alkenyl and —(C₂-C₆)alkynyl; and
R⁶ is R³ or R⁵.

In an embodiment of the invention, the formed ester is a compound of formula (IV):

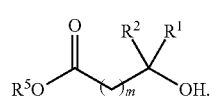

(IV)

In an embodiment of the invention, the formed ester is a compound of formula (IV); wherein m is equal to 0 or 1.

In a preferred embodiment of the invention, the formed ester is 2-ethyhexyllactate, 2-propylheptyllactate, di(2-ethylhexyl)tartrate, di(2-propylheptyl)tartrate, tri(2-ethylhexyl) citrate, tri(2-propylheptyl)citrate, 2-ethylhexylglyco late, 2-propylheptylglyco late, tri(2-ethylhexyl)isocitrate, tri(2-propylheptyl)isocitrate, 2-ethyhexylmandelate, 2-propylheptylmandelate, di(2-ethylhexyl)malate or di(2-propylheptyl)malate. When the ester of formula (IV) is a stereogenic carbon centre, the formed ester can be a D-ester, L-ester, meso-ester or a mixture thereof, wherein an L-ester is preferred.

In a preferred embodiment of the invention, the formed ester is 2-ethyhexyl-L-lactate.

The presence of the catalysts of the invention allows the esters of formula (III) to be obtained in higher yields.

Furthermore, it is possible to carry out the method at a lower temperature than a method according to the prior art.

The reaction of the carboxylic acid of formula (I) and a (C₁-C₃₆)alcohol can take place at a temperature of about 25-250° C., about 30-250° C., about 40-240° C., about 50-230° C., about 60-230° C., about 70-220° C., about 80-210° C., about 90-200° C., about 100-190° C. or about 100-180° C.

In a preferred embodiment of the invention, the reaction takes place at a temperature of about 50-220° C., more preferably about 100-180° C.

In an embodiment of the invention, the reaction takes place at a temperature of about 110° C., about 130° C. or about 150° C.

In an embodiment of the invention, the reaction takes place at a temperature of less than 180° C.

Although the reaction in the presence of the catalysts of the invention also proceeds almost to completeness without removal of the reaction products water and/or ester of formula (III), it can furthermore be helpful to remove the reaction products during the method from the equilibrium. To this end, among others, distillation or the use of a dephlegmator could be considered.

In an embodiment of the invention, the method comprises a distillation step by means of an increase of the temperature and/or a reduction of the pressure after and/or during the reaction of the carboxylic acid of formula (I) and a (C₁-C₃₆) alcohol in the presence of a catalyst.

In an embodiment of the invention, the method comprises a step of removing water and/or the formed ester of formula (III) from the reaction mixture after or during the reaction of the carboxylic acid and a (C₁-C₃₆)alcohol in the presence of a catalyst.

In an embodiment of the invention, water is removed during the reaction from the reaction mixture.

In an embodiment of the invention, (i) a carboxylic acid and the $(C_1-C_{36})$alcohol are provided and the reaction mixture is heated to a temperature $T^1$; and (ii) subsequently the catalyst is added.

In an embodiment of the invention, $T^1$ is a temperature, at which no or no significant reaction by autocatalysis occurs.

In an embodiment of the invention $T^1$ is between about 25-50° C., about 50-60° C., about 60-70° C., about 70-80° C., about 80-90° C., about 90-100° C., or about 100-110° C., preferably $T^1$ is about 110° C.

Furthermore, it can further be advantageous to preheat the reaction mixture in a first step before adding the catalyst of the invention to a temperature $T^1$ and to add the catalyst and react the carboxylic acid of formula (I) and the $(C_1-C_{36})$ alcohol at a temperature $T^2$ in a second step. Depending on the method, it can also be advantageous to preheat the carboxylic acid of formula (I) and the catalyst of the invention to a temperature $T^1$ in a first step and to add the $(C_1-C_{36})$alcohol and carry out the reaction at a temperature $T^2$ in a second step.

In an embodiment of the invention, (i) the carboxylic acid of formula (I) and the $(C_1-C_{36})$alcohol are provided and preheated to a temperature $T^1$; and (ii) the catalyst is subsequently added and the carboxylic acid of formulae (I) and the $(C_1-C_{36})$alcohol are reacted at a temperature $T^2$ (wherein $T^2 \geq T^1$) wherein the pressure is optionally reduced.

In an embodiment of the invention, (i) the carboxylic acid of formula (I) and the catalyst of the invention are provided and heated to a temperature $T^1$ and (ii) the $(C_1-C_{36})$alcohol is subsequently added and the carboxylic acid of formula (I) and the $(C_1-C_{36})$alcohol are reacted at a temperature $T^2$ ($T^2 \geq T^1$), wherein the pressure is optionally reduced.

In an embodiment of the invention, $T^2$ is between about 100-110° C., 110-250° C., 120-240° C., 130-230° C., 140-220° C., 150-210° C., 160-200° C. or 170-190° C.

In an embodiment of the invention $T^2$ is about 130° C., 150° C. or 180° C.

The invention inter alia provides an improved method of reacting carboxylic acids of formula (I) and $(C_1-C_{36})$alcohol to the corresponding esters of formula (III). It is possible to carry out the reaction with a low excess of the $(C_1-C_{36})$ alcohol at good yields.

In an embodiment of the invention, the molar ratio of the carboxylic acid of formula (I) to the $(C_1-C_{36})$alcohol is between about 1:1 and about 1:4, between about 1:1 and about 1:3, between about 1:1 and about 1:2, preferably between about 1:1 and about 1:2 (relative to a carboxyl function of the carboxylic acid of formula (I)).

In methods using carboxylic acids that have more than one carboxyl function it is necessary to adapt the molar ratio of the $(C_1-C_{36})$alcohol to the number of carboxyl functions in the carboxylic acid accordingly.

In an embodiment of the invention, the catalyst is used in a molar ratio relative to the carboxylic acid of formula (I) of about 0.001-5%, preferably about 0.05-2%.

In an embodiment of the invention, the carboxylic acid is reacted with at least two different $(C_1-C_{36})$alcohols.

If the used carboxylic acid of formula (I) is a hydroxyalkylcarboxylic acid of formula (II), the carboxylic acid of formula (I) can also be present in dimeric, trimeric and/or oligomeric form. Thus, for instance, lactic acid is present in a 88% aqueous solution as monomeric lactic acid (about 86.77 mol-%), dimer (about 11.26 mol-%) or trimer (about 1.98 mol-%) are present. When the reaction of lactic acid in the presence of a catalyst according to the present invention, such as 2-hydroxyethylsulfonic acid, the molar portion of the monomeric esters is 96.25% of the dimeric esters 3.62% and the trimeric esters 0.13%, the rest being oligomeric ester.

In an embodiment of the invention, the provided carboxylic acid of formula (VII)

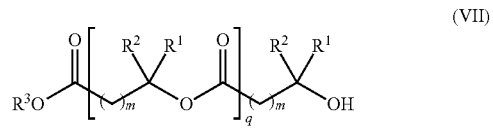

has a weight portion of monomeric carboxylic acid (q=0) relative to the total (monomeric (q=0), dimeric (q=1), trimeric (q=2) and oligomeric (q>2)) carboxylic acid of about 50-100%, preferably about 60-90%, more preferably about 70-80%.

In an embodiment of the invention, the employed carboxylic acid of formula (I) is provided as an aqueous solution, wherein the carboxylic acid is present in a weight portion of about 50-100%, about 60-100%, about 70-90%, about 85-90%, or about 88%.

In an embodiment of the invention, the formed ester is present in a weight portion of 80-100%, preferably 85-100%.

In an embodiment of the invention, the formed ester is present in a molar portion of 80-100%, preferably 85-100%.

In an embodiment of the invention, the weight portion of the formed esters of dimers, trimers and oligomers are about 0-10%, preferably between about 0-5%.

In an embodiment of the invention, the molar portions of the formed esters of the dimers, trimers and oligomers are between about 0-10%, preferably between about 0-5%, more preferably between 0-4%.

In an embodiment of the invention, the weight portion of the formed ester of the dimer is 0-10%, preferably 0-5%, more preferably 0-4%.

In an embodiment of the invention, the molar portion of the formed ester of the dimer is 0-10%, preferably 0-5%, more preferably 0-4%.

In an embodiment of the invention, the weight portion of the formed ester of the trimer is 0-1.5%, preferably 0-0.5%, more preferably 0-0.2%.

In an embodiment of the invention, the molar portion of the formed esters of the trimer is 0-1.5%, preferably 0-0.5%, more preferably 0-0.2%.

In an embodiment of the invention, the weight portion of the dimeric ester is reduced relative to the reaction without catalyst.

In an embodiment of the invention, the weight portion of the trimeric ester is reduced relative to the reaction without catalyst.

In an embodiment of the invention, the weight portion of the dimeric and trimeric ester is reduced relative to the reaction without catalyst.

The prefix "$C_x-C_y$" means the possible number of carbon atoms in the respective group.

The term "$(C_1-C_6)$alkyl", alone or as part of another group, means a linear aliphatic carbon chain containing 1 to 6 carbon atoms or a branched aliphatic carbon chain containing 4 to 6 carbon atoms. Non-limiting exemplary $(C_1-C_6)$alkyl groups comprise methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl und 1-ethyl-2-methylpropyl.

The term "$(C_1-C_{36})$alkyl", alone or as part of another group, means a linear or branched aliphatic saturated or unsaturated carbon group containing 1 bis 36 carbon atoms. Non-limiting exemplary $(C_1-C_{36})$alkyl groups comprise n-heptyl, n-octyl, 2-ethylhexyl, iso-octyl, nonyl, iso-nonyl, decyl, iso-decyl, cis-6-hexadenecene, 2-hexylethyl, and 2-proylheptyl.

The term "$(C_1-C_{36})$alcohol", as used herein means a $(C_1-C_{36})$alkyl group that is substituted with a —OH group.

The term "fatty alcohol" means a saturated or unsaturated $(C_6-C_{22})$alcohol. Non-limiting exemplary compounds comprise cis-9-hexadecene-1-ol, trans-9-octadecene-1-ol, cis-9-octadecene-1-ol, 1-decanol, 1-hexadecanol, 1-heptadecanol, 1-octadecanol, 2-propyl-4-methylhexanol, 2-propyl-5-methylhexanol, 2-isopropyl-4-methylhexanol, 2-isopropyl-5-methylhexanol, 2-propyl-4,4-dimethylhexanol, 2-ethyl-2-methylheptanol and 2-ethyl-2,5-dimethylhexanol.

The term "$(C_2-C_6)$alkenyl" means a linear or branched alkyl group having 2, 3, 4, 5 or 6 and one, two or three carbon-carbon double bonds. In one embodiment, the $(C_2-C_6)$alkenyl has one carbon-carbon double bond. Non-limiting exemplary $(C_2-C_6)$alkenyl groups comprise vinyl (ethenyl), 1-propenyl, 1-butenyl, 2-butenyl, 3-butenyl, 1-pentenyl and 1-hexenyl.

The term "$(C_2-C_6)$alkynyl" means a linear or branched alkyl group having one, two or three carbon-carbon triple bonds. In one embodiment the $(C_2-C_6)$alkynyl has one carbon-carbon triple bond. Non-limiting exemplary $(C_2-C_6)$alkynyl groups comprise ethynyl, 1-propynyl, 2-butynyl, 1-pentynyl and 1-hexynyl.

The term "$(C_6-C_{10})$aryl" means mono- or bicyclic aromatic compounds having 6 to 10 carbon atoms. Non-limiting exemplary $(C_6-C_{10})$aryl groups comprise phenyl, isonaphthyl and naphthyl.

The term "halogen" or "halo" comprises the group consisting of —F, —Cl, —Br und —I.

The term "about" in relation to a measurable dimension relates to normal variations in the measured value, which depend on the accuracy of the measuring equipment or are expected by the skilled person as a result of statistical variations. Typically, the variation is ±10%, preferably ±5%

A compound is referred to as catalyst which is not (significantly) consumed during the reaction, but accelerates the formation of a product of a reaction.

Within the framework of the present application, the term "carboxylic acid" means a compound having a $COOR^3$ functional group, wherein $R^3$ can be —H or —$(C_1-C_6)$alkyl. If $R^3$ is —H and the carboxylic acid furthermore has a —OH functional group in the alkyl chain, a hydroxyalkylcarboxylic acid is present (wherein the —COOH group does not comprise the —OH functional group).

The term "hydroxyalkylcarboxylic acid" means a carboxylic acid that also has a —OH functional group in the alkyl chain. Hydroxyalkylcarboxylic acids can be present along with their monomeric form (q=0; see formula (VII)) in the form of a dimer (q=1), trimer (q=2) or oligomer (q>2) as a result of intermolecular esterification:

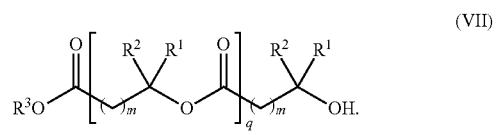

(VII)

The term "salt" means a chemical compound that is formed by reaction of an acid with a base. The salt can be provided in anhydrous form (anhydrate) or in the form of a hydrate. Hydrate salts contain water molecules in a specific ratio which are either bonded to the metal centre or are crystallised with the crystal complex. The depiction "salt× $nH_2O$", gives the number n of the water molecules per salt molecule. "n" is usually a number 1-12, wherein fractions may occur. Salts can be present as double salts, i.e. as salts comprising two or more different cations and/or anions which crystallise in the same regular crystal structure.

The term "weight portion" (also referred to "mass portion") means the portion of the respective component relative to the sum of all components measured by weight, provided that no other basis is given. The term "molar portion" means the amount of substance fraction of the respective component relative to the sum of all components measured by weight, provided that no other basis is given. The sum of all components of the reaction do not comprise the unreacted $(C_1-C_{36})$alcohol, the catalyst and/or water, but relate to the monomeric, dimeric, trimeric and oligomeric carboxylic acid as well as the monomeric, dimeric, trimeric and oligomeric ester and optionally further by-products.

EXAMPLES

The employed lactic acid was obtained by means of a fermentation process as a 88 wt.-% aqueous solution. The results of an analysis of the composition of the lactic acid are shown in Table 1.

TABLE 1

| Composition of the starting material lactic acid 88% | | | | |
|---|---|---|---|---|
| | Monomeric lactic acid | Dimeric lactic acid | Trimeric lactic acid | Oligomeric lactic acid |
| Wt.-% | 75.65 | 17.67 | 4.48 | 2.2 |
| Mol % | 86.77 | 11.26 | 1.98 | n.b. | n.b. = not calculated

Comparative Example 1

890 g 2-ethylhexanol and 445.5 g aqueous lactic acid solution (88 wt.-%) are heated to 180° C. under a stream of $N_2$ and the mixture is stirred for 210 min. The content of 2-ethylhexyllactate adjusted for residual amounts of 2-ethylhexanol is 80.53%. Table 2 describes the composition of the obtained 2-ethylhexyllactate.

TABLE 2

Portion of the raw product 2-ethylhexyllactate without
distillation of excess (by autocatalysis)

|  | Monomeric lactic acid | Dimeric lactic acid | Trimeric lactic acid | Oligomers/ others |
|---|---|---|---|---|
| Wt.-% | 1.01 | 0.41 | 0.24 | 0.89 |
| Mol % | 2.38 | 0.53 | 0.21 | n.b. |

|  | 2-ethylhexyllactate | -dilactate | -trilactate | -tetralactate |
|---|---|---|---|---|
| Wt.-% | 80.53 | 13.73 | 2.58 | 0.61 |
| Mol % | 84.38 | 10.61 | 1.58 | 0.31 |
| Total Mol % | 86.76 | 11.14 | 1.79 | n.b. | n.b. = not calculated

Example 2

890 g 2-ethylhexanol and 445.5 g lactic acid solution (88 wt.-%) are heated to 110° C. under a stream of $N_2$. The catalyst tin-bis(2-ethylhexanoate) (12.82 g) is added and the temperature is increased to 180° C. and the mixture is stirred for 380 min. The content of 2-ethylhexyllactate adjusted for residual amounts of 2-ethylhexanol is 90.5%.

Example 3

890 g 2-ethylhexanol and 445.5 g lactic acid solution (88 wt.-%) are heated to 110° C. under a stream of $N_2$. The catalyst 2-hydroxyethanesulfonic acid (18.31 g of a 70 wt.-% aqueous solution) is added and the temperature is increased to 180° C. and the mixture is stirred for 270 min. The content of 2-ethylhexyllactate adjusted for residual amounts of 2-ethylhexanol is 90.0%.

Example 4

890 g 2-ethylhexanol and 445.5 g lactic acid solution (88 wt.-%) are heated to 110° C. under a stream of $N_2$. The catalyst aluminiummesylate (12.82 g) is added, the temperature is increased to 180° C. and the mixture is stirred for 260 min. The content of 2-ethylhexyllactate adjusted for residual amounts of 2-ethylhexanol is 90.8%.

Example 5

890 g 2-ethylhexanol, 445.5 g lactic acid solution (88 wt.-%) and the catalyst 2-hydroxyethanesulfonic acid (9.16 g of a 70 wt.-% solution) are heated to 110° C. under a stream of $N_2$ and the mixture is stirred for 240 min. The content of 2-ethylhexyllactate adjusted for residual amounts of 2-ethylhexanol is 90.0%.

Example 6

890 g 2-ethylhexanol, 445.5 g lactic acid solution (88 wt.-%) and the catalyst 2-hydroxyethanesulfonic acid (0.9 g of a 70 wt.-% aqueous solution) are heated to 130° C. under a stream of $N_2$ and the mixture is stirred for 390 min. Determination of the acid value (AV) gives 0.29 mg/g. The content of 2-ethylhexyllactate adjusted for residual amounts of 2-ethylhexanol is 87.4%.

Example 7

445.5 g of lactic acid solution (88 wt.-%) and the catalyst 2-hydroxyethanesulfonic acid (0.9 g of a 70 wt.-% aqueous solution), are heated to 85° C. under a stream of $N_2$. 890 g of 2-ethylhexanol are added and the mixture is heated to 130° C. under a stream of $N_2$ and the mixture is stirred for 480 min. A dephlegmator (set to 110° C.) is used during the reaction. The content of 2-ethylhexyllactate adjusted for residual amounts of 2-ethylhexanol is 88.6%.

Example 8

770 g of 2-ethylhexanol and 386 g of lactic acid solution (88 wt.-%) and the catalyst 2-hydroxyethanesulfonic acid (15.8 g of a 70 wt.-% aqueous solution) are heated to 130° C. under a stream of $N_2$ and the mixture is stirred for 160 min. The content of 2-ethylhexyllactate adjusted for residual amounts of 2-ethylhexanol is 91.82%.

TABLE 3

Portion of the raw product 2-ethylhexyllactate without distillation
of excess according to Experiment 8

|  | Monomeric lactic acid | Dimeric lactic acid | Trimeric lactic acid | Oligomers/ others |
|---|---|---|---|---|
| Wt.-% | 0.41 | 0.03 | 0 | 2.85 |
| Mol % | 0.96 | 0.04 | 0 | n.b. |

|  | 2-ethylhexallactate | -dilactate | -trilactate | -tetralactate |
|---|---|---|---|---|
| Wt.-%% | 91.82 | 4.68 | 0.21 | 0 |
| Mol % | 95.29 | 3.58 | 0.13 | 0 |
| Total Mol % | 96.25 | 3.62 | 0.13 | n.b. | n.b. = not calculated

The invention claimed is:
1. A method of preparing an ester by reacting a carboxylic acid of formula (I):

$$R^3O \underset{O}{\overset{\displaystyle\|}{C}} \text{---}(\ )_m\text{---}\underset{R^1}{\overset{R^2}{C}}\text{---}R^0; \qquad (I)$$

wherein
R⁰ is —H or —OR³;
R¹ is —H, —(C₁-C₆)alkyl, —(C₁-C₆)alkylCOOR³, —COOR³ or —OR³;
R² is —H, —(C₁-C₆)alkyl, —(C₁-C₆)alkylCOOR³ or (C₆-C₁₀)aryl, wherein R² is optionally substituted with —OR³ and/or —COOR³;
R³ is —H;
m is 0, 1, 2, 3, 4 or 5;
with a (C₁-C₃₆)alcohol;
wherein the reaction is carried out in the presence of a catalyst,
wherein the catalyst is selected from the group consisting of 1-hydroxyethanesulfonic acid, 2-hydroxyethanesulfonic acid, and aluminiummesylate,
wherein the (C₁-C₃₆)alcohol is a C₆-C₃₆ Guerbet alcohol of formula (VI):

$$\text{(VI)}$$

wherein
p is 0 to 15; and
wherein the reaction takes place at a temperature of 50-220° C.

2. The method according to claim 1, wherein the carboxylic acid is a hydroxyalkyl acid of formula (II):

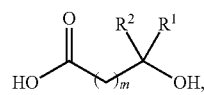

(II)

and $R^1$ and $R^2$ are as defined in claim 1.

3. The method according to claim 1, wherein the carboxylic acid of formula (I) is selected from the group consisting glycolic acid, lactic acid, tartaric acid, citric acid, isocitric acid, mandelic acid, and malic acid.

4. The method according to claim 1, wherein the carboxylic acid is present in the D-configuration, L-configuration, meso-configuration or as a mixture of these configurations.

5. The method according to claim 1, wherein the formed ester is a compound of formula (III):

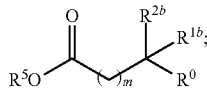

(III)

wherein
$R^0$ is —H or —$OR^3$;
$R^{1b}$ is —H, —($C_1$-$C_6$)alkyl, —($C_1$-$C_6$)alkylCOOR$^6$, —COOR$^6$ or —$OR^3$;
$R^{2b}$ is —H, —($C_1$-$C_6$)alkyl or —($C_1$-$C_6$)alkylCOOR$^6$, wherein $R^{2b}$ is optionally substituted with —$OR^3$ and/or —COOR$^6$;
$R^5$ is —($C_1$-$C_{36}$)alkyl;
$R^6$ is $R^3$ or $R^5$.

6. The method according to claim 1, wherein the formed ester is a compound of formula (IV):

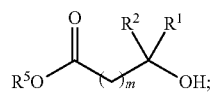

(IV)

wherein
$R^5$ is —($C_1$-$C_{36}$)alkyl.

7. The method according to claim 1, wherein the ($C_1$-$C_{36}$)alcohol is 2-ethylhexanol or 2-propylheptanol.

8. The method according to claim 1, wherein the weight portion of a monomer of the carboxylic acid is about 50-100%.

9. The method according to claim 1, characterized in that the molar ratio of carboxylic acid and ($C_1$-$C_{36}$)alcohol is between about 1:1 and about 1:3.

10. The method according to claim 1, wherein the catalyst is present in a molar ratio relative to the carboxylic acid of about 0.001-5%.

11. The method according to claim 1, wherein the catalyst is present in a weight ratio relative to the carboxylic acid of about 0.001-5%.

12. The method according to claim 1, which comprises a step of distillation by increasing the temperature and/or reducing pressure after and/or during the reaction of the carboxylic acid with a ($C_1$-$C_{36}$)alcohol in the presence of a catalyst.

13. The method according to claim 1, wherein the carboxylic acid is L-lactic acid;
the ($C_1$-$C_{36}$)alcohol is 2-ethylhexanol; and
the catalyst is 2-hydroxyethanesulfonic acid.

14. The method according to claim 3, wherein the carboxylic acid of formula (I) is lactic acid.

15. The method according to claim 4, wherein the carboxylic acid is present in the L-configuration.

* * * * *